US008613774B2

(12) United States Patent
Bartel et al.

(10) Patent No.: US 8,613,774 B2
(45) Date of Patent: Dec. 24, 2013

(54) ELBOW REPLACEMENT APPARATUS AND METHODS

(75) Inventors: Donald L. Bartel, Ithaca, NY (US); Mark P. Figgie, Riverside, CT (US); Robert N. Hotchkiss, Riverside, CT (US); Joseph D. Lipman, New York, NY (US); Darrick Lo, Greenbrook, NJ (US); Timothy M. Wright, New York, NY (US)

(73) Assignee: New York Society for the Ruptured and Crippled maintaining the Hospital for Special Surgery, New York, NY (US)

( * ) Notice: Subject to any disclaimer, the term of this patent is extended or adjusted under 35 U.S.C. 154(b) by 243 days.

(21) Appl. No.: 12/947,506

(22) Filed: Nov. 16, 2010

(65) Prior Publication Data

US 2011/0125274 A1   May 26, 2011

Related U.S. Application Data

(60) Provisional application No. 61/261,575, filed on Nov. 16, 2009.

(51) Int. Cl.
*A61F 2/38*   (2006.01)
(52) U.S. Cl.
USPC ................... 623/20.12; 623/20.13

(58) Field of Classification Search
USPC ............................ 623/20.11–20.13
See application file for complete search history.

(56) References Cited

U.S. PATENT DOCUMENTS

| 4,383,337 | A | * | 5/1983 | Volz et al. ................. 623/20.12 |
| 6,027,534 | A |   | 2/2000 | Wack et al. |
| 6,379,387 | B1 |  | 4/2002 | Tornier |
| 6,699,290 | B1 |  | 3/2004 | Wack et al. |
| 6,890,357 | B2 |  | 5/2005 | Tornier |
| 7,247,170 | B2 |  | 7/2007 | Graham et al. |
| 7,449,028 | B2 |  | 11/2008 | Ball |
| 2003/0144739 | A1 | | 7/2003 | Huene |
| 2006/0100712 | A1 | | 5/2006 | Ball |
| 2006/0173546 | A1 | * | 8/2006 | Berelsman et al. ........ 623/20.11 |
| 2008/0033566 | A1 | | 2/2008 | Berelsman et al. |

* cited by examiner

*Primary Examiner* — David H Willse
*Assistant Examiner* — Javier Blanco
(74) *Attorney, Agent, or Firm* — Leason Ellis LLP

(57) ABSTRACT

Apparatus and methods for total elbow replacement are provided to allow a surgeon to intraoperatively select a linked or unlinked constraint by utilizing a connection located on the body of the ulnar and/or humeral stem. Additional modularity also allows the selection of a cemented or cementless stem as described herein. The modularity and adjustability provides a number of advantages.

10 Claims, 23 Drawing Sheets

ELBOW REPLACEMENT APPARATUS AND METHODS

CROSS REFERENCE TO RELATED APPLICATION

The present application claims the benefit of U.S. patent application Ser. No. 61/261,575, filed Nov. 16, 2009, which is hereby incorporated by reference in its entirety.

TECHNICAL FIELD

The present invention relates to prosthetic joints and more particularly, to an elbow implant system that has an articular surface designed to gradually shift a contact point between components outwardly as the joint undergoes varus/valgus rotation and further includes a modular construction to allow for the surgeon to select different components for use depending upon the particular application and/or observations.

BACKGROUND

Joint arthroplasty is the most successful treatment thus far for relieving pain and restoring function to patients suffering from arthritis and other destructive joint problems. Hip and knee replacements are quite common with more than half a million of each procedure performed annually in the US. The popularity of hip and knee arthroplasty has been established by the efficacy and durability of these types of joint replacements. For example, the Australian national registry reports cumulative revision rates of only 4% at seven years for primary total knee arthroplasty, while the Swedish national registry reports survivorships of greater than 93% at 10 years for hip arthroplasty. For total elbow replacement, the results are not as good, with the Norwegian Arthroplasty Register reporting a failure rate of 8% and 15% at 5- and 10-year follow up, respectively.

The two leading clinical indications for total elbow arthroplasty are rheumatoid arthritis and posttraumatic arthritis. The two primary elbow replacement types used to treat these arthritic events are constrained and unconstrained designs, also referred to as linked and unlinked, respectively. Linked elbow replacements have intrinsic stability as the humeral and ulnar components are mechanically connected to one another, usually by a hinge. Some laxity exists to permit a small degree of varus-valgus and internal-external rotational movements. The humeral and ulnar components in unlinked elbow replacements, however, are not mechanically connected. For these implants, the degree of varus-valgus and internal-external rotational movements are dependent primarily on the quality of ligamentous and muscular integrity.

In the past, an unlinked elbow has been introduced with a porous coating on the fixation surfaces of the humeral and ulnar components. However, a study showed that of 32 elbow replacement arthroplasties in the test group (32 cementless humeral components, 4 cementless ulnar components), only one patient showed a radiolucent line around the humeral component after an average 3-year follow up. No radiolucent lines were exhibited around the ulnar components.

Currently, there are several devices for elbow replacement. The Coonrad-Morrey total elbow arthroplasty (TEA) system employs linked components, including polyethylene bushings on the humeral and ulnar components through which a metal axle passes, and an anterior flange on the humeral component used in conjunction with bone graft to increase torsional and anteroposterior stability in vivo. The humeral and ulnar components are cemented into place. The hinge permits ±3.5° of varus-valgus motion, with the intent that the load will be transferred to the soft tissues before max angulation is achieved.

Recent studies have evaluated the success of the Coonrad-Morrey TEAs and in particular, one study evaluated 67 Coonrad-Morrey TEAs. Of these, 37 were primary arthroplasties with a five-year survival rate of 72%. The remaining 30 were revision arthroplasties, which had a five-year survivorship of 64%. Other studies have reported ten-year survival of 51% and fifteen-year survival of 24%. Clinical results have only rivaled hip and knee replacement in less active patients, such as those with rheumatoid arthritis. For this group, implant survivorship is about 90% at five to ten years.

An implant-related failure mode with the Coonrad-Morrey TEA is wear and deformation of the polyethylene bushings, causing both decreased function of the joint as the bushing-axle constraint decreases and osteolysis secondary to the release of large volumes of polyethylene wear particles. Studies have reported radiographic evidence of bushing wear in three of six patients after less than five years, requiring patients to undergo revision surgery. Similarly, another study reported bushing wear as the cause of failure in ten patients, all of whom required revision surgery an average of five years postoperatively. A study has shown that 1% of their patients required revision surgery for an isolated bushing exchange at an average of eight years after their TEA. In yet another study, components retrieved from sixteen elbows in fourteen patients were examined and found that damage to the humeral and ulnar polyethylene bushings was nearly universal with asymmetrical thinning and elliptical plastic deformation. Metallic wear on the fixation stem of the ulnar component, consistent with loosening at the implant-cement interface, was observed in most of the cases, underscoring the additional problem of aseptic loosening in TEAs.

The Discovery Elbow System from Biomet, Inc. is a linked, cemented total elbow replacement. The hinge has an hourglass shape to maximize articular surface contact between the humeral and ulnar components. Minimal bone resection maintains the integrity of the humeral epicondyles. The device preserves the ulnar collateral ligament.

The Latitude Total Elbow Prosthesis from Tornier is a modular, cemented total elbow replacement. This device is designed to restore the normal kinematics of the elbow joint creating a modular spool that allows the surgeon to adjust the central, posterior, and anterior offset of the joint axis. A second articular component can be attached to the ulnar component to convert from unlined to linked. The device also has an optional radial component. Limitations of using the Latitude include the complete dissection of the distal humerus that is required for implantation of the components, the use of multiple jigs to locate the natural joint axis that may not be present in a patient with rheumatoid arthritis, limited triceps split to gain access to the ulnar canal, and the use of cemented components.

However, none of these devices allow for intraoperative adjustment of soft tissue tension. For the unlinked condition, conventional devices do not provide for mechanical constraint to varus/valgus motion. It would be desirable to produce an elbow replacement with an articular surface designed to gradually shift the contact point outwardly as more varus/valgus motion is initiated, thus increasing the restoring moment at the joint. It would also be desirable to provide apparatus and methods for total elbow replacement that allow a surgeon to intraoperatively select a linked or unlinked constraint, accommodate cemented or cementless fixation, as well as adjust soft tissue tension of the joint.

SUMMARY

In accordance with the present invention, apparatus and methods for total elbow replacement are provided to allow a surgeon to intraoperatively select a linked or unlinked constraint by utilizing a connection located on the body of the ulnar and/or humeral stem. Additional modularity also allows the selection of a cemented or cementless stem as described herein. The modularity and adjustability provides a number of advantages.

In one embodiment, an elbow prosthesis includes a humeral stem component having a distal end and a proximal end. The prosthesis also includes a humeral condyle (condylar) component having a distal end and a proximal end, with the proximal end of the humeral condyle component being adapted to attachably engage the distal end of the humeral stem component. The distal end of the humeral condyle component includes distally extending portions.

An ulnar stem component is provided and has a distal end and a proximal end. The ulnar stem component tapers from the proximal end to the distal end. The ulnar bearing component is adapted to attachably engage the proximal end of the ulnar stem component and the distally extending portions of the humeral condyle component.

In another embodiment, an elbow prosthesis includes a humeral stem component and an humeral condyle component associated with the humeral stem component. The humeral condyle component has distally extending portions that define condyle bearing surfaces. The prosthesis also includes an ulnar stem component and an ulnar bearing component associated with the ulnar stem component. The ulnar bearing component has bearing surfaces that receive and engage the distally extending portions of the humeral condyle component. Each of the condyle bearing surfaces and the bearing surfaces of the ulnar bearing component has a cross-section in a coronal plane that exhibits at least two different radii such that varus or valgus rotation of the humeral condyle component relative to the ulnar bearing component causes a contact point between the condyle bearing surface and the bearing surfaces of the ulnar bearing component to move outwardly (laterally).

In another embodiment, an elbow prosthesis includes a humeral implant having a stem and a humeral condyle portion disposed at an end of the stem. The humeral condyle portion includes distally extending portions. The prosthesis also includes an ulnar stem component having a distal end and a proximal end. The ulnar stem component is tapered from the proximal end to the distal end. An ulnar bearing component that is a separate component relative to the ulnar stem component is detachably coupled to the proximal end of the ulnar stem component and the distally extending portions of the humeral condyle portion. This modularity of the ulnar implant permits a common ulnar stem to be used with an ulnar bearing component that is either of a linked type or an unlinked type.

These and other aspects, features and advantages shall be apparent from the accompanying Drawings and description of certain embodiments of the invention.

BRIEF DESCRIPTION OF THE DRAWINGS

A few exemplary embodiments of the invention are depicted in the following figures, in which.

DETAILED DESCRIPTION OF EXEMPLARY EMBODIMENTS

Apparatus and methods for total elbow replacement as described herein allow a surgeon to intraoperatively select a linked or unlinked constraint by utilizing a connection located on the body of the ulnar and/or humeral stem. The elbow system can be either of a linked type or unliked type in that a humeral component can either be linked to an ulnar component or they can be unlinked and free of attachment. Additional modularity also allows the selection of a cemented or cementless stem as described herein.

Figure 1:
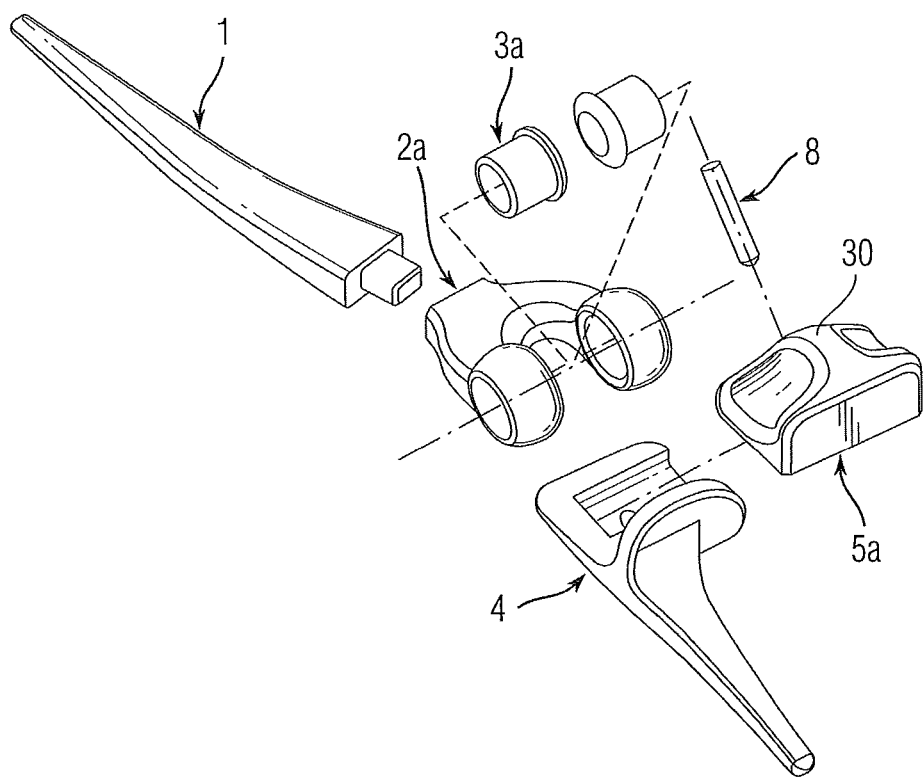
FIG. 1 provides a perspective view of an illustrative modular, unlinked elbow replacement device in accordance with some embodiments of the disclosed subject matter, FIG. 2 provides a perspective view of an illustrative modular, linked elbow replacement device in accordance with some embodiments of the disclosed subject matter, FIG. 3A provides a perspective view of an illustrative non-modular, non-cemented humeral component in accordance with some embodiments of the disclosed subject matter, FIG. 3B provides a perspective view of a non-modular, cemented humeral component in accordance with some embodiments of the disclosed subject matter, FIG. 3C provides a perspective view of a non-cemented humeral component with lateral recess in accordance with some embodiments of the disclosed subject matter, FIG. 4 provides perspective views of a non-cemented humeral sleeve in accordance with some embodiments of the disclosed subject matter, FIG. 5 provides a perspective view of a modular, humeral condyle component in accordance with some embodiments of the disclosed subject matter, FIG. 6 provides a perspective view of an alternate non-cemented, modular humeral stem design in accordance with some embodiments of the disclosed subject matter, FIG. 7 provides a perspective view of an articulation-adjustable ulnar component in linked state in accordance with some embodiments of the disclosed subject matter, FIG. 8 provides a perspective view of an alternate, non-cemented ulnar stem design in accordance with some embodiments of the disclosed subject matter, FIG. 9 provides a perspective view of an articulation-adjustable ulnar component in unlinked state in accordance with some embodiments of the disclosed subject matter, FIG. 10 provides a perspective view of an ulnar stem and unlinked ulnar bearing in accordance with some embodiments of the disclosed subject matter, FIG. 11 provides a perspective view of an ulnar stem, linked ulnar bearing, and linked ulnar bearing housing in accordance with some embodiments of the disclosed subject matter.
Figure 2:
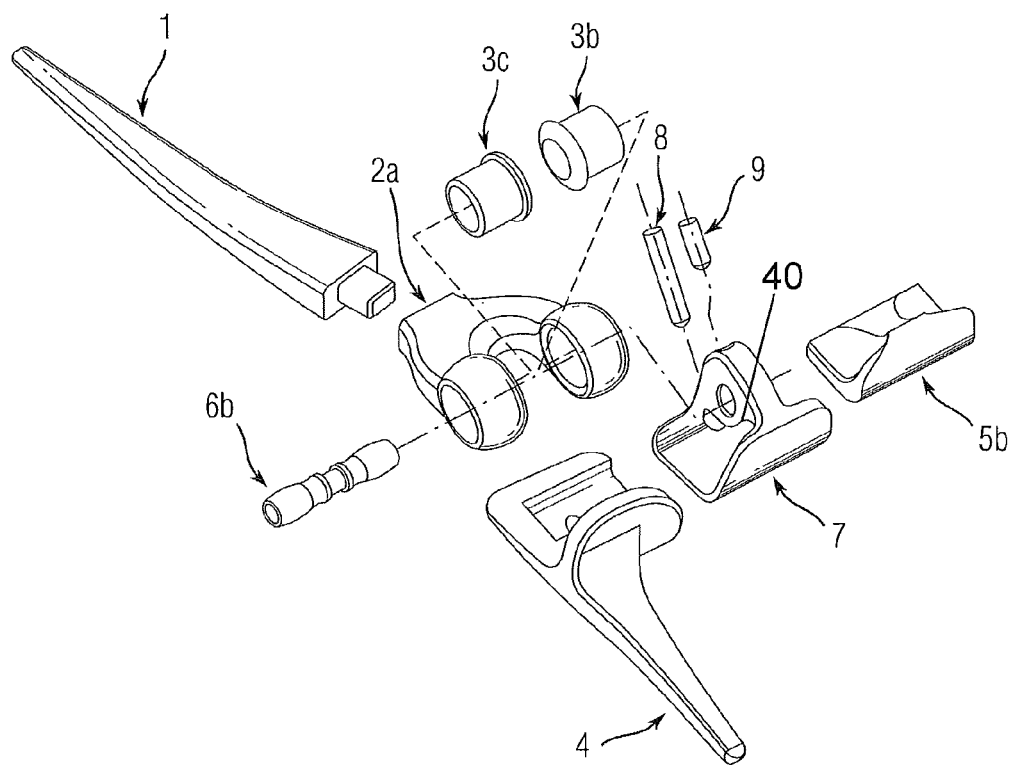

A modular total elbow replacement in accordance with some embodiments of the disclosed subject matter is shown in its unlinked and linked versions in FIGS. 1 and 2, respectively.

Non-modular, Non-cemented Humeral Component Configuration

Figure 3A:
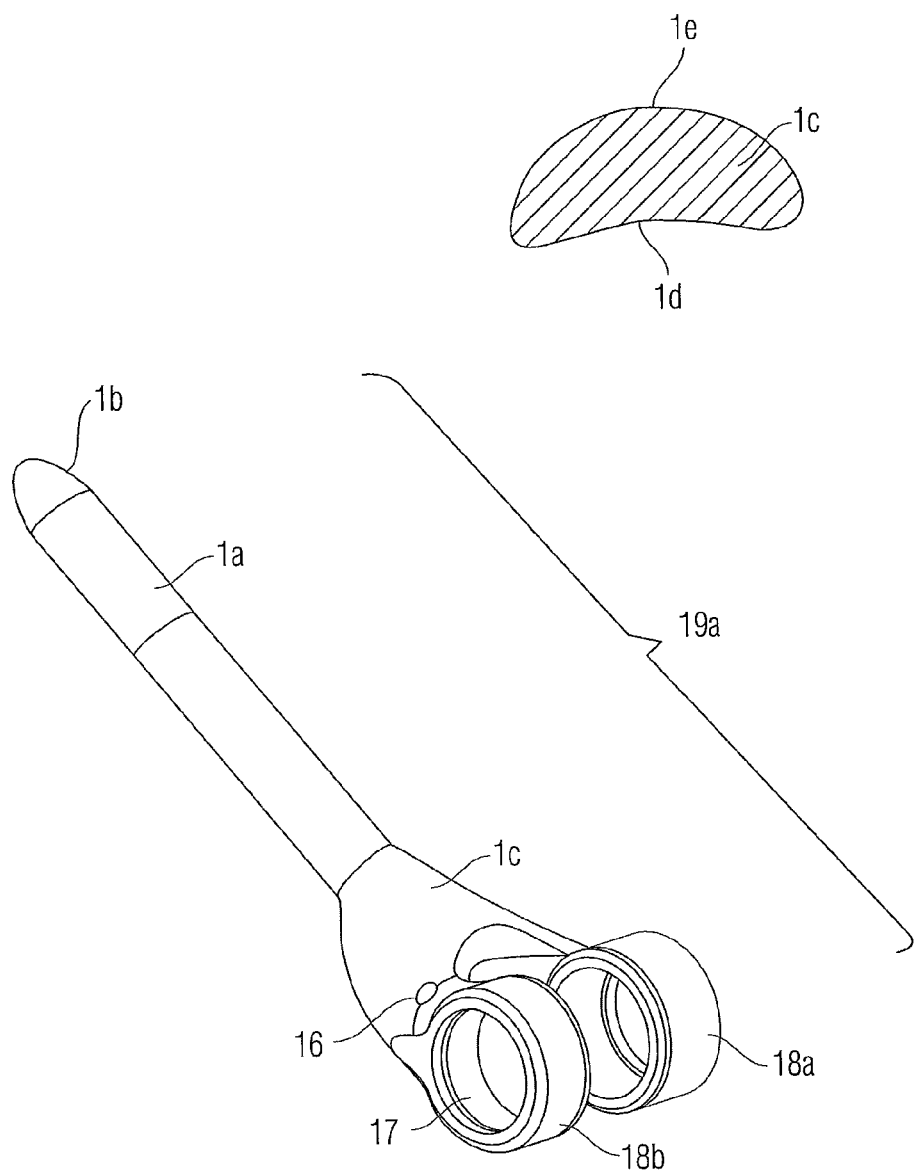
Figure 3B:
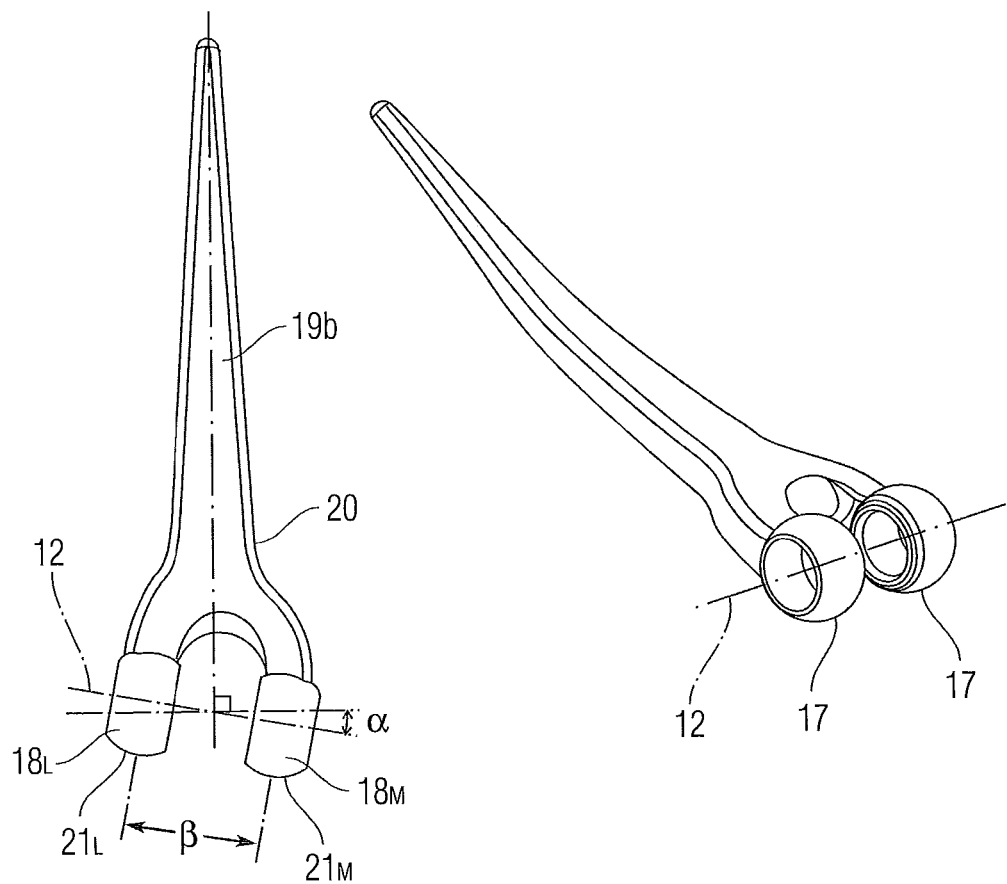

In some embodiments of the disclosed subject matter, the humeral component 19a may be non-modular and non-cemented as illustrated in FIG. 3A. In this geometry, the proximal stem 1a is a curved cylinder. The proximal end of stem 1a has a bullet shaped tip 1b to improve the distribution of load on the bone. The mid-portion geometry 1c of the humeral component 19a curves anteriorly to approximately follow normal anatomy of the humerus. The mid-portion geometry 1c has a posterior concavity 1d that interacts with olecranon fossa and an anterior convexity 1e creating a chevron-like cross-section, and is tapered medial-laterally to transfer load to the humerus as distally as possible. The outer surface of the mid-portion 1c may be coated with plasma spray or porous metal and possibly hydroxyapatite to promote cementless fixation to bone. The distal end of the humeral component 19a has two extending bodies (medial $18_M$ and lateral $18_L$ condyles) that are separated by distance β as shown in FIG. 3B. In most instances, $18_M$ will have a greater width ($W_{Mh}$) than $18_L$ ($W_{Lh}$) (FIG. 14A), improving load transfer on the medial side. The medial $18_M$ and lateral $18_L$ condyles have convex surfaces $21_{M,L}$ that contact corresponding concave unlinked ulnar bearing 5a and linked ulnar bearing 5b. The contact is non-conforming. The condyles $18_{M,L}$ each have a cylindrical hole 17 that shares an axis 12 (the implant joint axis) that may or may not be perpendicular td the long axis of the proximal end of the humeral component 19a.

Figure 3C:
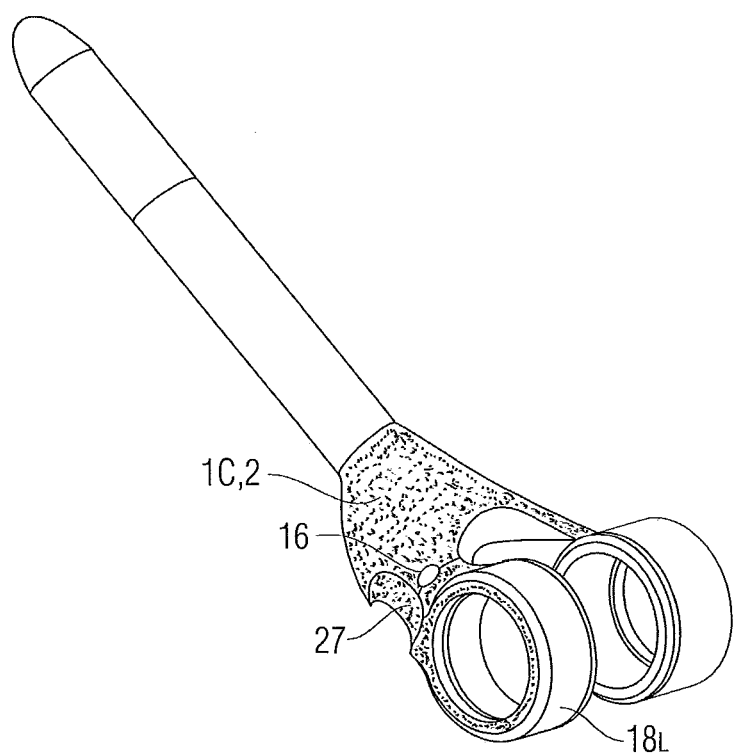

The holes 17 accept either press-fit humeral bushings 3b,c or bushing hole caps 3a. The humeral component 19 can have a built-in carry angle α as shown in FIG. 3B. The humeral component 19 can have suture holes 16 (FIGS. 3A and 3C) on the medial and lateral side for soft tissue/bone attachment. On the postero-lateral aspect of mid-portion geometry 1C adjacent to condyle $18_L$, there can be a recess 27 to contain any lateral bone fragments caused by an avulsion fracture for example. The recess 27 will protect the fixation of said fragments from shear loads when used in conjunction with sutures which pass through suture holes 16. It will be appreciated that plasma spray or porous coating around suture holes 16, recess 27, and mid-portion geometry 1c as seen in shaded regions in FIG. 3C will promote bone ingrowth.

Non-modular, Cemented Humeral Component Configuration

In some embodiments of the disclosed subject matter, the humeral component 19b, as seen in FIG. 3B, can be cemented into bone. The shape of the distal end of component 19b can be identical to component 19a. The shape of the cemented region of the humeral component 19b can be similar to embodiments shown in FIG. 3A but can be reduced in size to create room for cement (for example, ~1 to 2 mm thick cement mantle), have a rectangular or triangular cross-section for rotational stability, and have radii 20 on respective corners to reduce stress in the bone cement. There is no porous coating on the cemented component.

Humeral Sleeve

Figure 4:
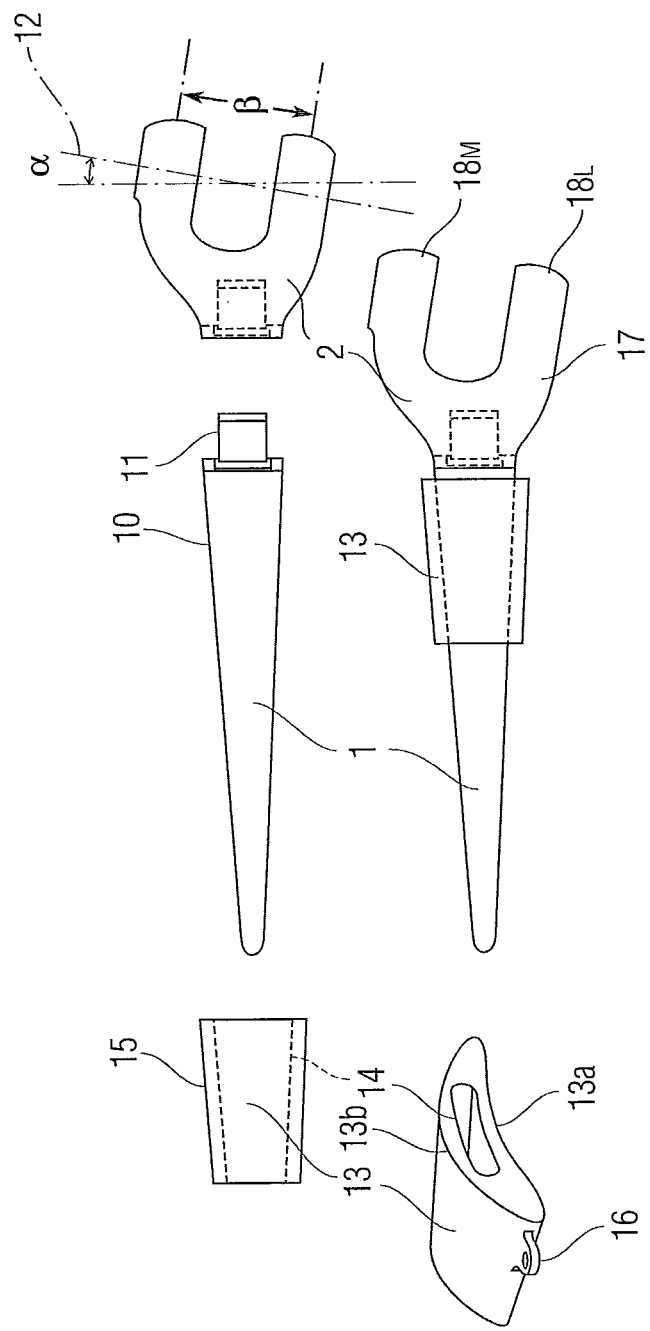

In some embodiments of the disclosed subject matter, the mid-portion geometry 1c of the humeral component 19a can be substituted with a humeral sleeve 13, as illustrated in FIG. 4. The sleeve has an inner geometry 14 that mates with the body 10. The outer surface 15 of sleeve 13 can be coated with plasma spray or porous metal and possibly hydroxyapatite to promote cementless fixation to bone. The transverse outer cross-section of the sleeve 13 has a posterior concavity 13a that interacts with olecranon fossa and an anterior convexity 13b creating a chevron to improve implant-bone contact, and is tapered medial-laterally to transfer load to the humerus as distally as possible. The elbow replacement system can include a number of humeral sleeves of different geometries such that the surgeon can select the sleeve most suited for the patient's intramedullary anatomy. Sleeve 13 can have suture holes 16 to allow a surgeon to pass sutures through the implant to attach soft tissues to the implant, thus providing additional joint stability. Sleeve 13 can be used with modular or non-modular humeral component.

Modular Humeral Component Configuration

Figure 5:
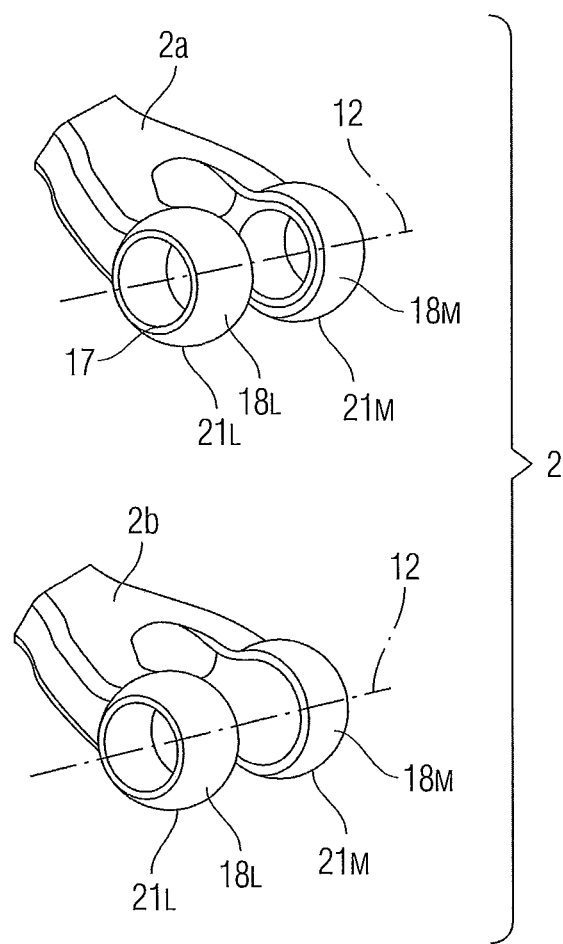

An alternative embodiment for a non-cemented and cemented humeral component design is illustrated in FIG. 4 in accordance with some embodiments of the disclosed subject matter. The humeral condyle component 2 mates with humeral extending body 11 from the humeral stem 1, thereby establishing modularity in both linked and unlinked elbow systems. The distal end of the component 2a has a geometry identical to the distal end of humerl component 19b as illustrated in FIG. 5. The unlinked elbow system can also use a humeral condyle component 2b which is identical to component 2a except that it does not have the cylindrical holes 17. Component 2 can have a built-in carry angle α.

The humeral condyle component 2 can have suture holes 16 (FIG. 3C) on the medial and lateral side for soft tissue/bone attachment. On the postero-lateral aspect of component 2 adjacent to condyle $18_L$, there can be a recess 27 to contain any lateral bone fragments. It will be appreciated that plasma spray or porous coating around suture holes 16, recess 27, and component 2 as seen in shaded regions in FIG. 3C will promote bone ingrowth.

Figure 6:
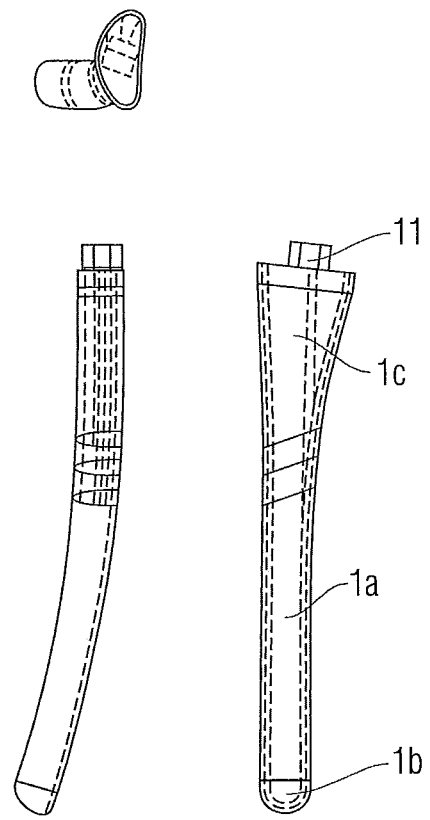

The elbow replacement system can have humeral condyle components 2 of various geometries should the surgeon want to adjust the carrying angle, the constraint, and/or the condylar geometries. The humeral stem 1 can be cementless as illustrated in FIG. 6, with a curved cylinder proximal stem 1a, bullet tip 1b, a mid-portion geometry 1c that is plasma sprayed or porous coated, and a distal extending body 11 for engagement with condyle component 2. Similarly, the mid-portion geometry 1c can be substituted with humeral sleeve 13, as illustrated in FIG. 4. The humeral stem 1 can also be cemented with a rectangular or triangular cross-section for rotational stability, and have radii on respective corners to reduce stress in the bone cement. In addition, the modularity at extending body 11 permits revision without the need to remove a well-fixed humeral stem 1 from the bone canal should, for example, the condylar surfaces be worn or damaged.

The modularity of the humeral implant components thus permits a surgeon to interchange and match one humeral stem with one humeral condyle portion. Based on this feature, a hospital can predominantly stock one model of a humeral stem and a wider assortment of humeral condyle portions or vice versa. This allows greater savings by being able to stock less components as well as offering greater versatility as well as allow less components to be potentially used since an implanted stem remain in place while only the bearing component is replaced.

Articulation Adjustable Ulnar Component Configuration

Figure 7:
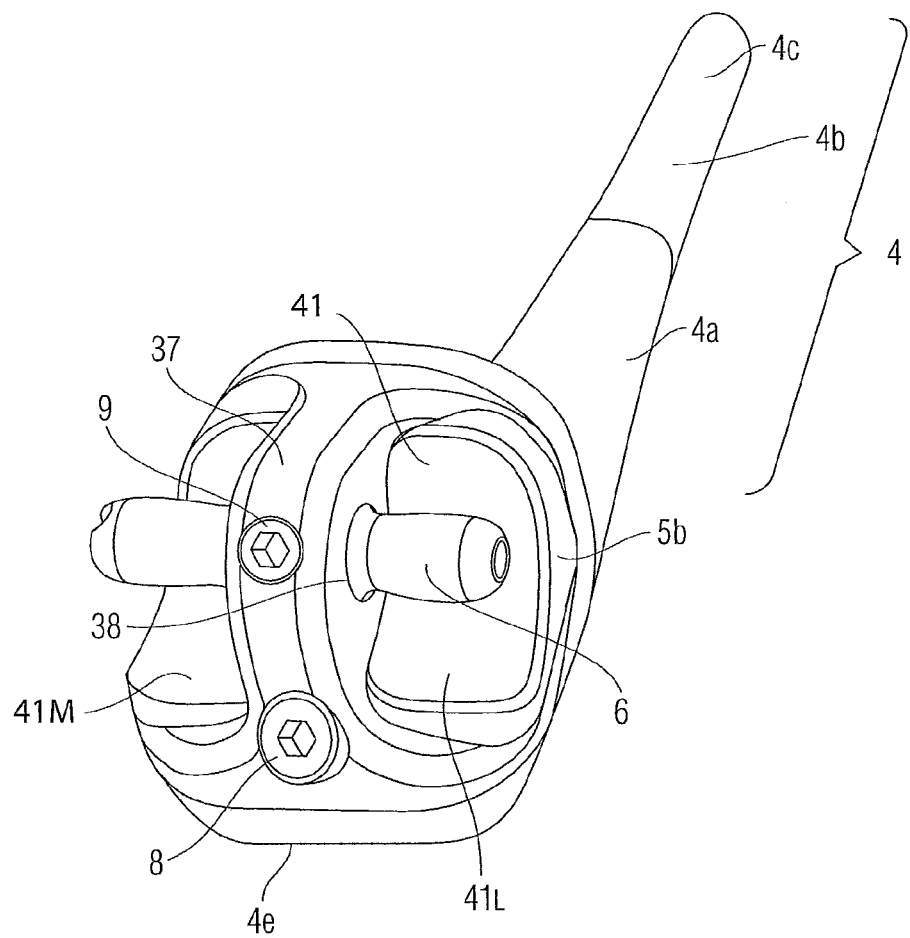
Figure 8:
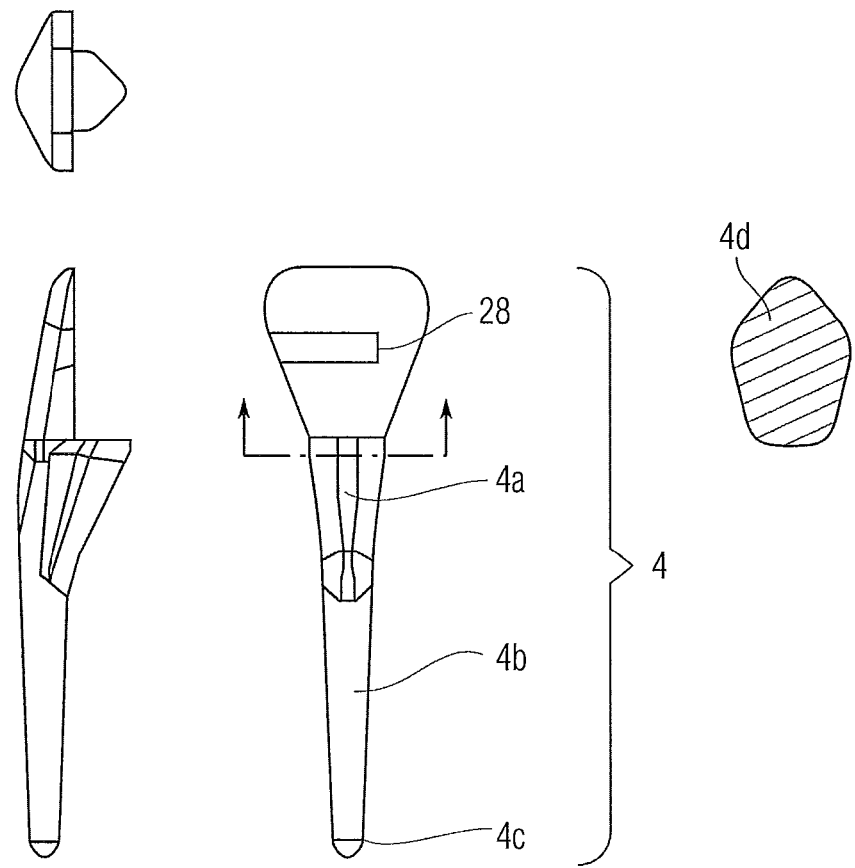

As illustrated in FIGS. 7 and 8, a non-cemented, articulation-adjustable ulnar stem 4 has a distal stem 4b that is conical in shape and terminates with a bullet shaped tip 4c to improve the distribution of load on the bone. The mid-portion body 4a has a medial/lateral and anterior/posterior and proximal/distal wedge and is approximately pentagonal in cross-section 4d where the apex interacts with the coronoid process to provide rotational stability. The proximal body has a large flat posterior surface 4e to resist additional rotational moments about the stem axis. The proximal body 29 of ulnar stem 4 has a sliding capture mechanism 28 that interacts with an unlinked ulnar bearing 5a (FIG. 1) or a linked ulnar bearing housing 7 (FIG. 2) inserted from approximately a medial and/or lateral direction establishing and adjustable articulation.

Figure 9:
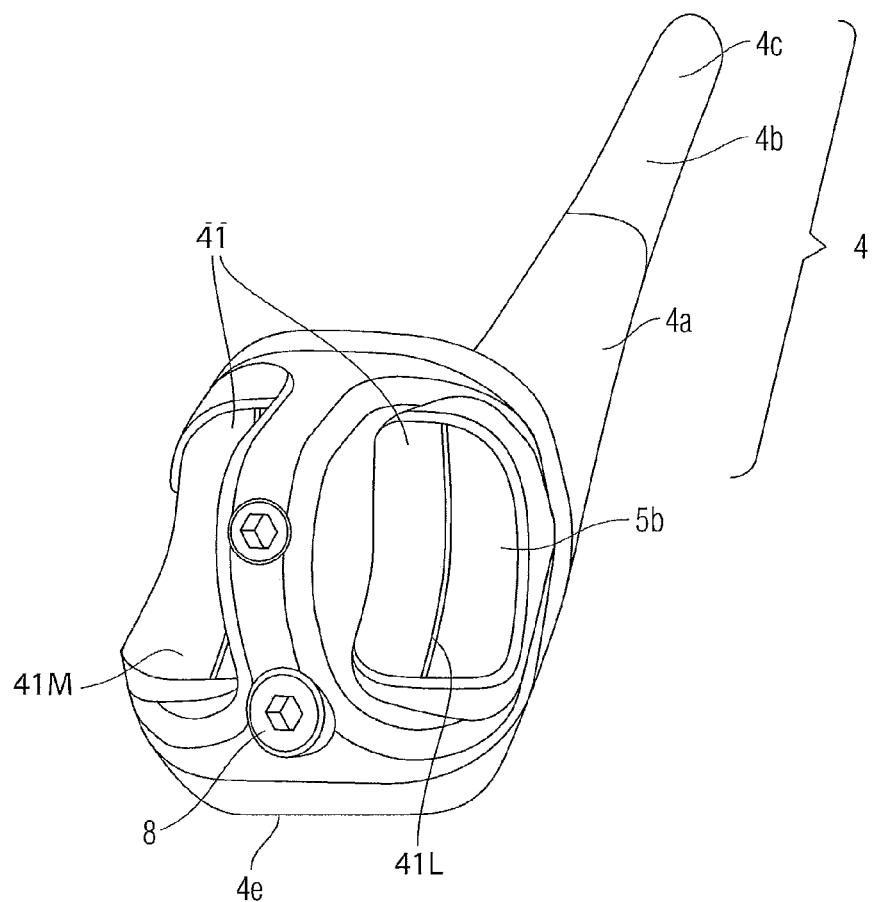

The capture mechanism 28 permits the selection of appropriately sized component, revision of worn components and/or facilitates conversion between unlinked and linked components as required. In the unlinked state as illustrated in FIG. 9, capture mechanism 28 interacts with engagement feature 33 (FIG. 10) on unlinked ulnar bearing 5a. In the linked state, capture mechanism 28 interacts with engagement feature 39 on linked ulnar bearing housing 7 (FIG. 11).

As used herein, the term ulnar bearing component at least includes an ulnar bearing that is configured to receive and engage the distally extending portions (condyles) of the humeral condlye component. As described herein, the ulnar bearing component can be of an unlinked or linked configuration. In the case of an unlinked configuration, the ulnar bearing can directly engage the ulnar stem. In the case of a linked configuration, the ulnar bearing component can include another member (housing or substrate) that supports the ulnar bearing and is adapted to engage the ulnar stem.

Unlinked Ulnar Bearing Component

Figure 10:
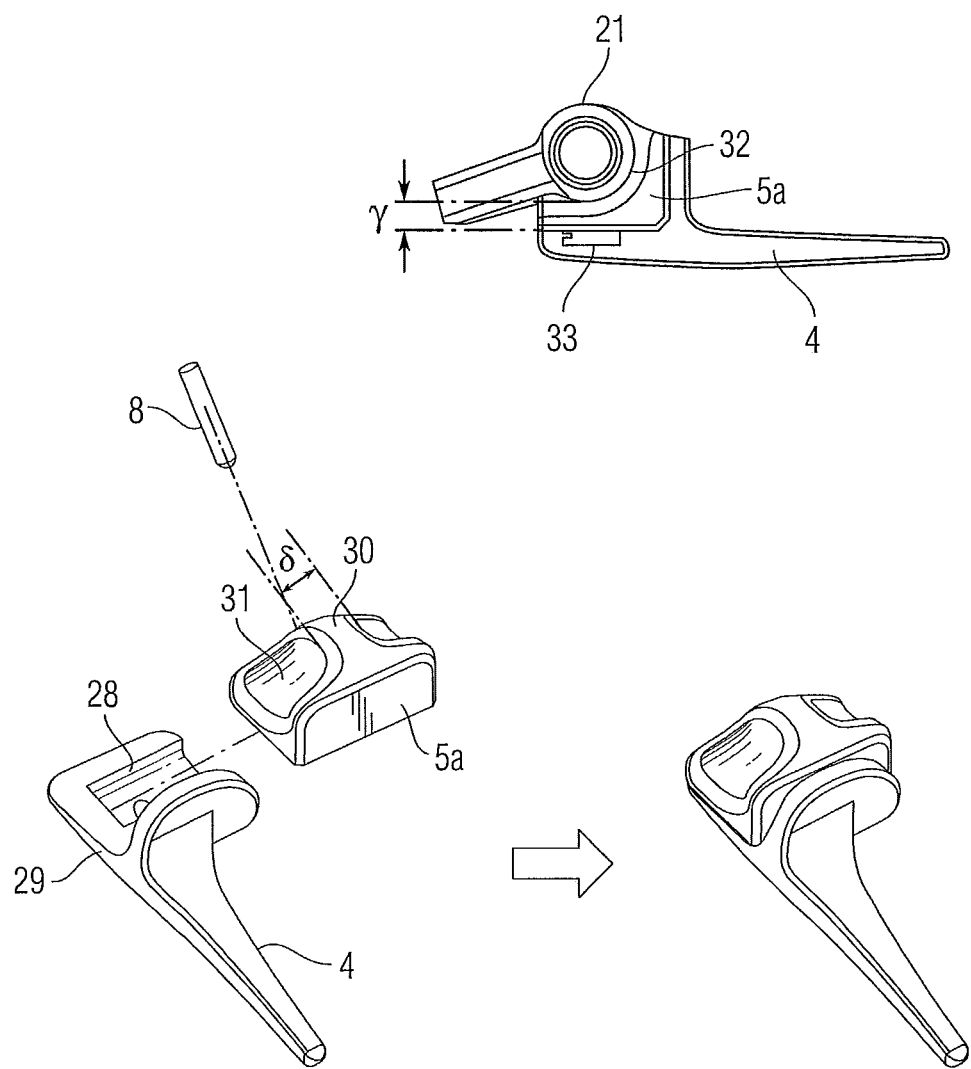
Figure 11:
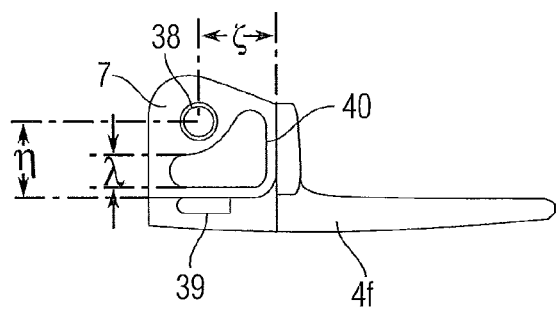
Figure 11:
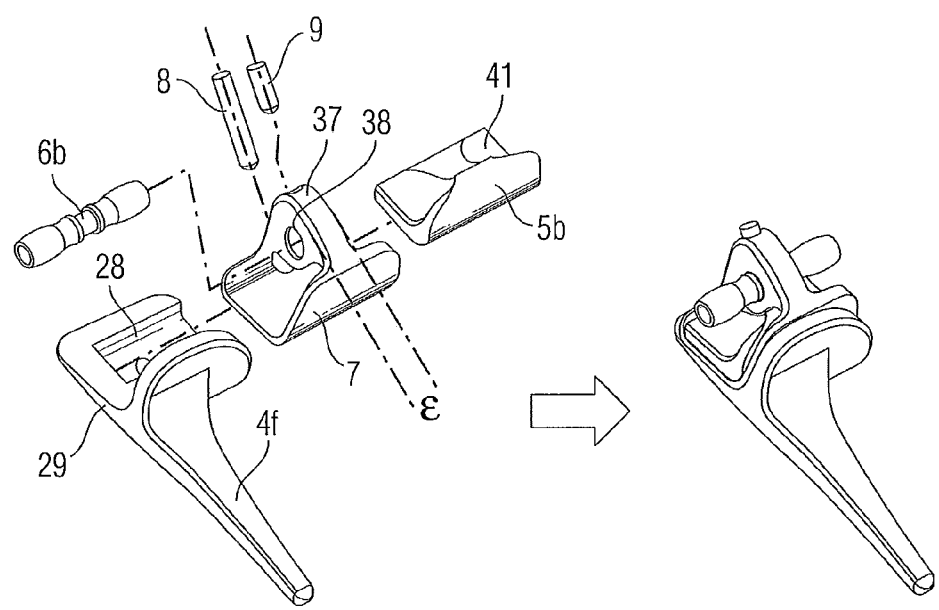

An unlinked ulnar bearing 5a, as illustrated in FIG. 10, for example, has an engagement feature 33 that interacts with the sliding capture mechanism 28 of the ulnar stem 4 and that can be inserted from approximately the medial and/or lateral direction. The bearing 5a can be rigidly locked to the stem 4 using, for example, a locking component 8. The unlinked ulnar bearing 5a has two concave surfaces $31_{M,L}$ that articulate with the convex humeral condyles $18_{M,L}$. The medial surface $31_M$ may have a greater width ($W_{Mu}$) than lateral surface $31_L$ ($W_{Lu}$) (FIG. 14B), improving load transfer on the medial side. The articulation is non-conforming. The bearing 5a also has a central post 30 that provides medial-lateral stability and a raised, distal articular face 32 to resist posterior dislocation of the ulna in flexion (FIGS. 9 and 10). The post 30 may be rectangular or trapezoidal in shape. The articulation-adjustability of ulnar stem 4 allows a surgeon to select ulnar bearings 5a of varying sizes/options defined by post thickness δ and/or bearing thickness γ for intra-operative adjustment of the degree of constraint, and/or various post alignments to adjust carry angle. The unlinked ulnar bearing 5a may be made of a low friction material, for example, ultra-high molecular weight polyethylene (UHMWPE).

Linked Ulnar Bearing Component

A linked ulnar bearing housing 7, as illustrated in FIG. 11, has an engagement feature 39 that interacts with the sliding capture mechanism 28 of the ulnar stem 4. The housing 7 has a central post 37 that provides medial-lateral stability of the linked elbow system. The housing 7 has a first opening 40 to accept a linked ulnar bearing 5b from a medial and/or lateral direction. The linked ulnar bearing 5b has two concave surfaces $41_{M,L}$ that articulate with the convex humeral condyles $18_{M,L}$. The medial surface $41_M$ may have a greater width ($W_{Mu}$) than lateral surface $41_L$ ($W_{Lu}$.) (FIG. 14B), improving load transfer on the medial side. The articulation is non-conforming. The bearing 5b can either be rigidly locked to central post 37 using, for example, a locking component 8, or act as a sliding platform with respect to central post 37. Should the bearing 5b need to be replaced, it can be removed from a medial or lateral direction. The linked ulnar bearing 5b may be made of a low friction material, for example, ultra-high molecular weight polyethylene (UHMWPE). The elbow replacement system provides various housing options. The post thickness ε and/or bearing thickness λ options permit intra-operative adjustment of the degree of constraint. The post 37 has a second opening 38 for axle 6. The axle hole 38 location option allows the surgeon to adjust anterior-posterior η and/or superior-inferior ζ offset of the joint axis 12. The axle 6 can be assembled from the medial and/or lateral direction to the central post 37 in vivo. The axle 6 can be rigidly locked to housing 7 using, for example, a locking component 9. The central portion 6c of axle that mates with housing 7 can have a D-shaped cross-section to prevent rotation about the joint axis 12. The central portion 6c may have a stop to prevent the central portion from advancing beyond central post 37. The ends 34 of the axle articulate with the inner diameters of the humeral bushings 3b,c.

The cemented ulnar stem 4f (FIG. 11) will have a similar shape to the non-cemented ulnar component 4 (FIG. 8) proximally, but may have a rectangular or triangular cross-section with rounded edges in the mid-4a and distal portion 4b and be reduced in size to create room for cement (for example, ~1 to 2 mm thick cement mantle).

Non-confirming Articulation Between Humeral and Ulnar Bearing Components

Figure 12:
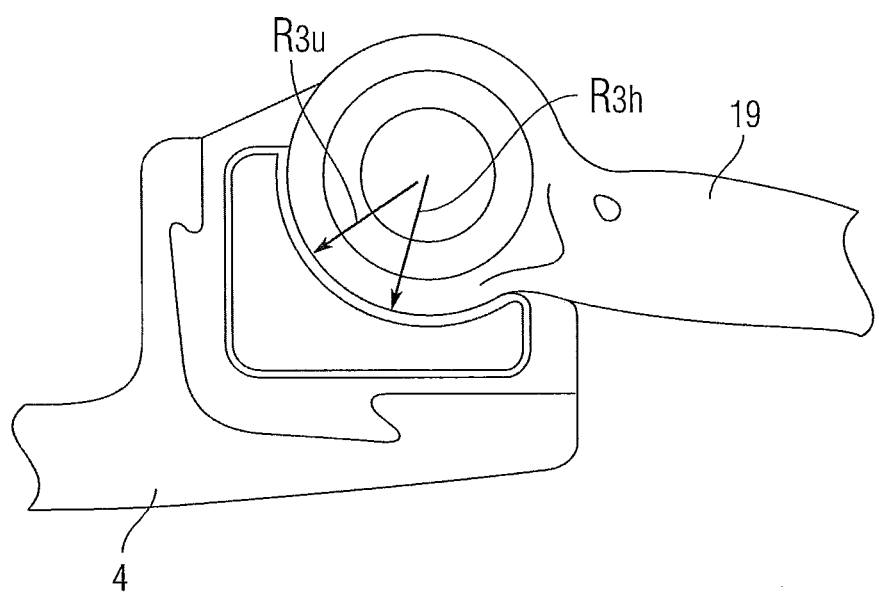
FIG. 12 illustrates differences in articular geometry between the humeral condyles and ulnar bearing surfaces in accordance with some embodiments of the disclosed subject matter.

The articulation between the humeral condyles $18_{M,L}$ and ulnar bearings 5a,b is not completely conforming in the sagittal plane ($R_{3h} < R_{3u}$) as illustrated in FIG. 12. The ratio of $R_{3h}/R_{3u}$ is approximately 0.95.

Figure 13:
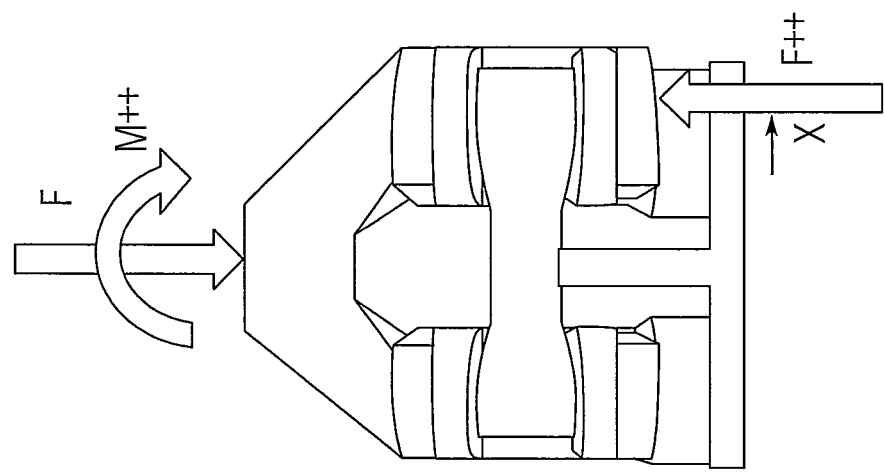
FIG. 13 illustrates a shift in contact point at articulation as external moment is applied in accordance with some embodiments of the disclosed subject matter.
Figure 13:
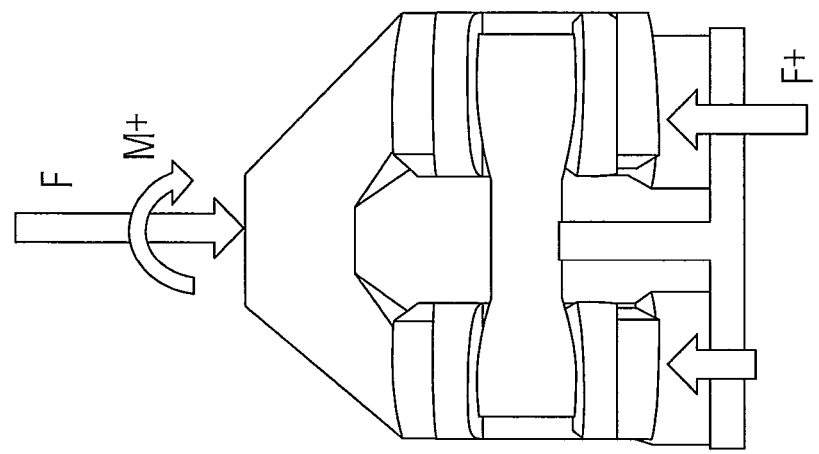
Figure 13:
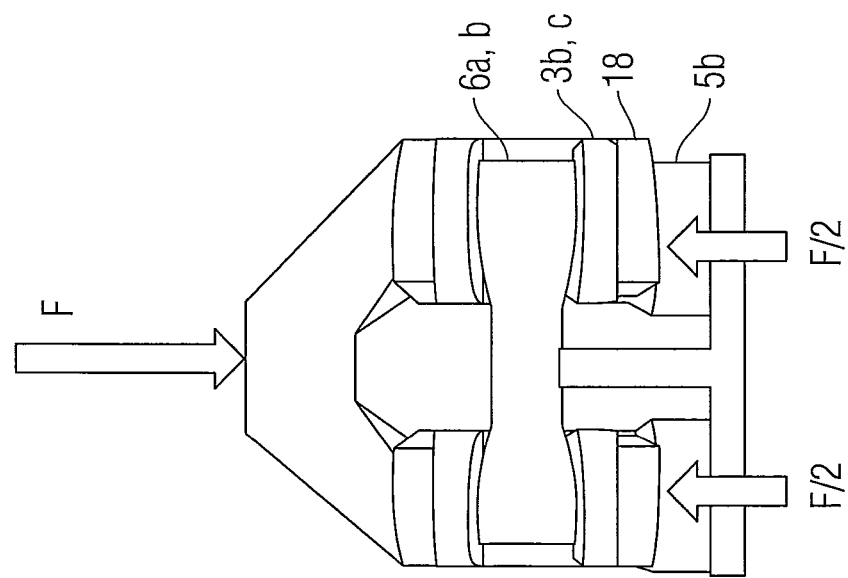
Figure 14A:
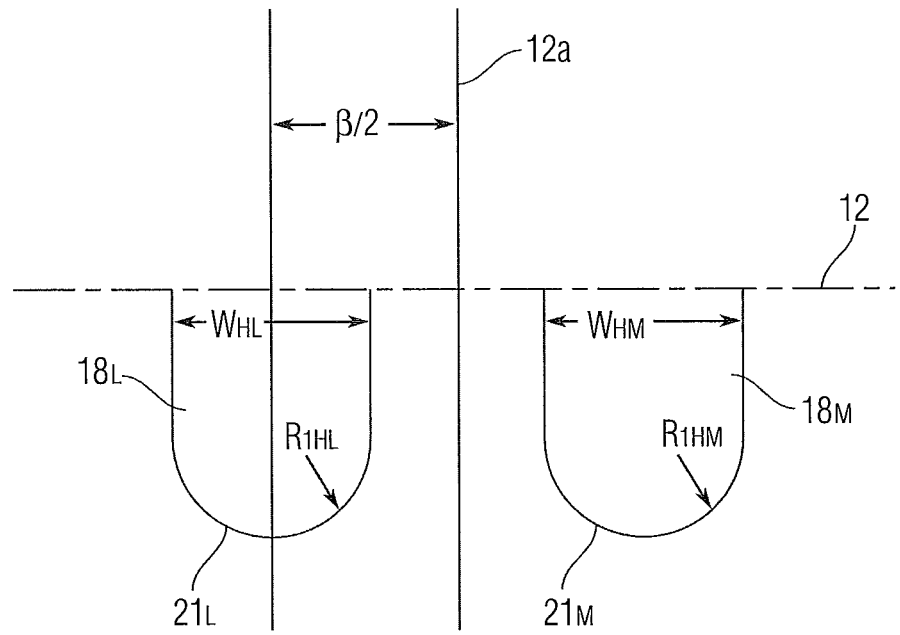
FIG. 14A illustrates differences in articular geometry of the humeral condyles in accordance with some embodiments of the disclosed subject matter.
Figure 14A:
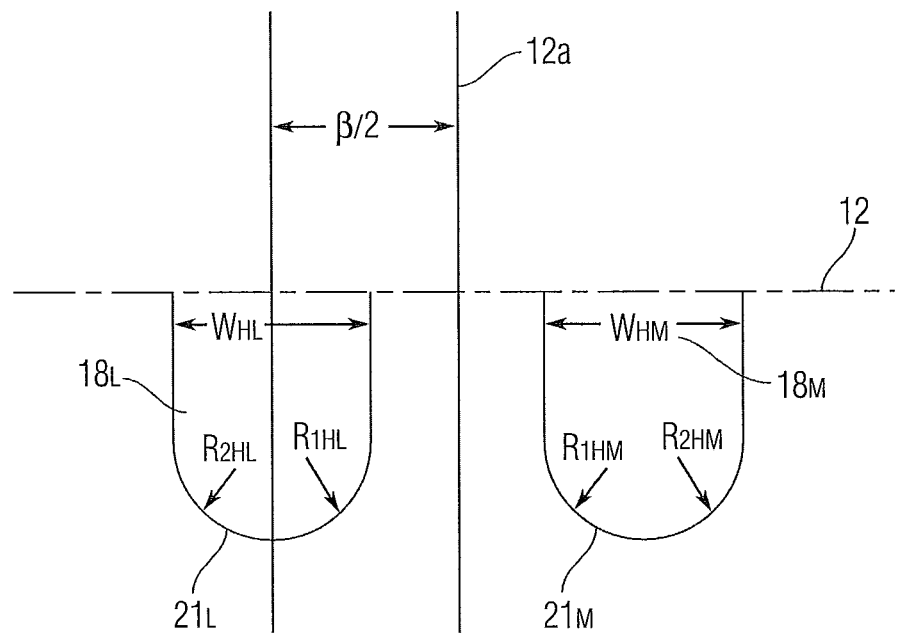
Figure 14B:
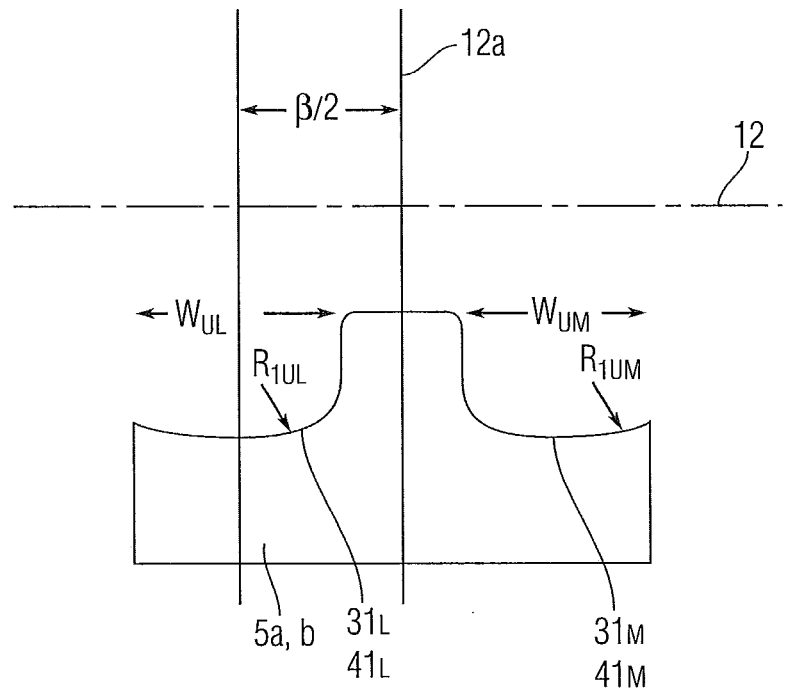
FIG. 14B illustrates differences in articular geometry of the ulnar bearing surfaces in accordance with some embodiments of the disclosed subject matter.
Figure 14B:
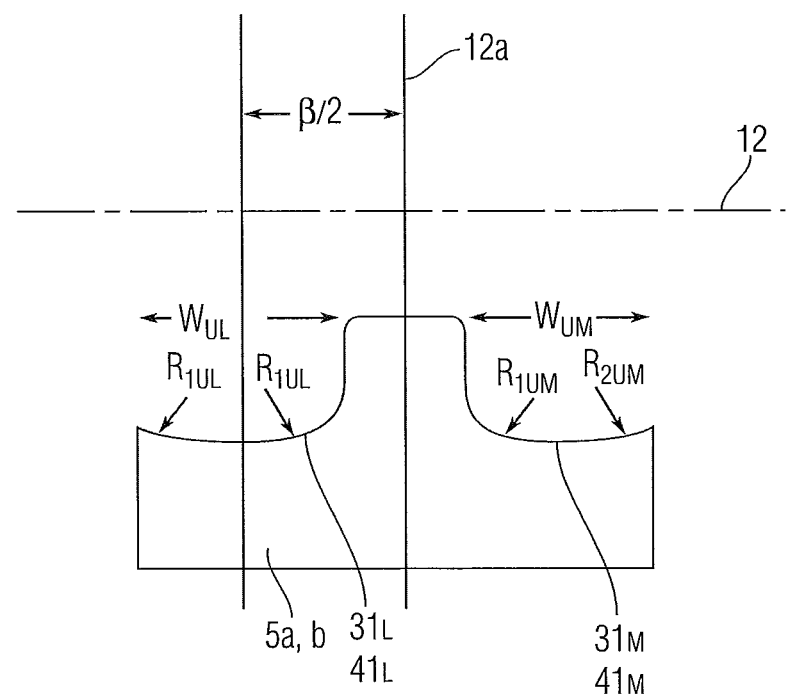
Figure 14C:
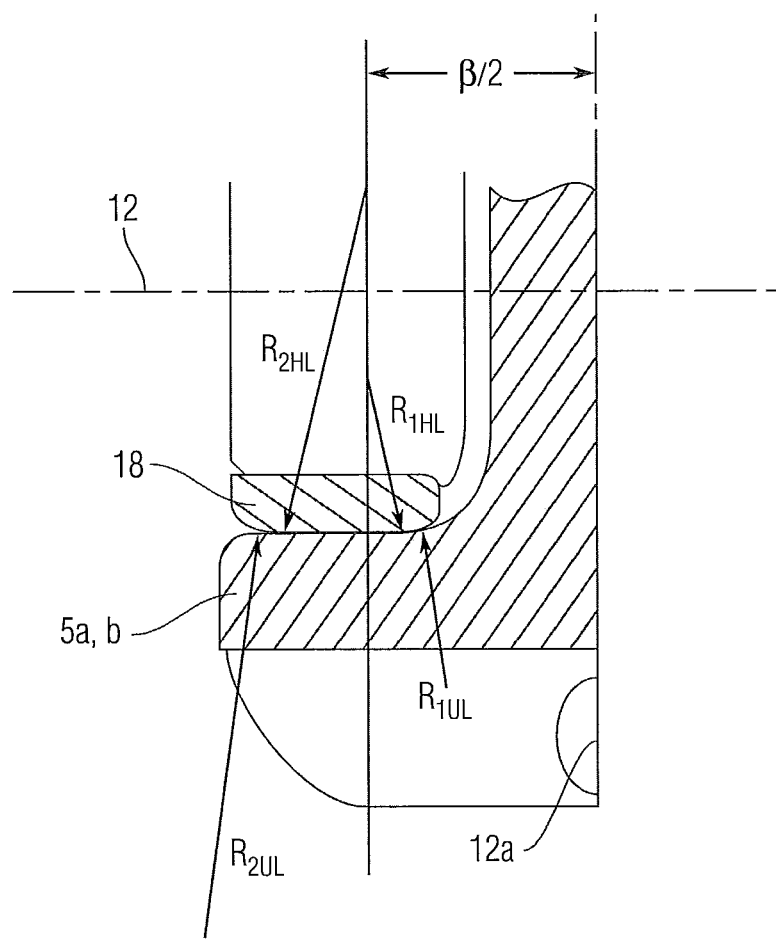
FIG. 14C illustrates the articulation between the humeral and ulnar components in accordance with some embodiments of the disclosed subject matter, FIG. 15 provides perspective views of a bushing hole cap and bushings in accordance with some embodiments of the disclosed subject matter, FIG. 16 provides a sectional view of a humeral bushing and axle in accordance with some embodiments of the disclosed subject matter, FIG. 17 provides a sectional view of an elbow joint in varus-valgus state in accordance with some embodiments of the disclosed subject matter, FIG. 18 provides sectional views illustrating articulation of the bushing hole cap and bushings of FIG. 15 in accordance with some embodiments of the disclosed subject matter, and FIG. 19 provides a perspective view of a radial head component in accordance with some embodiments of the disclosed subject matter.

The articulation between the humeral condyles $18_{M,L}$ and ulnar bearings 5a,b in the coronal plane is not completely conforming as seen in FIGS. 13 and 14C. The humeral condyle articular surfaces $21_{M,L}$ has a principal axis of rotation as defined by joint axis 12 as seen in FIGS. 14A,B,C. The articular surface $21_L$ is created by revolving a single radius $R_{1HL}$ about axis 12 creating a convex surface. Thus, in one embodiment, the articular surface $21_L$ and $21_M$ can be defined by the same radius (i.e., $R_{1HL} = R_{1HM}$) (see FIG. 14A).

An alternative embodiment of articular surface $21_L$, as illustrated in FIGS. 14A and 14C, similarly has a principal axis, but instead has two different radii $R_{1HL}$ (near midline 12a) and $R_{2HL}$ (away from midline 12a) that tangentially meet at a distance β/2 away from midline 12a. Radii $R_{1HL}$ and $R_{2HL}$ are revolved around joint axis 12 to create a convex surface. In other words, the bearing surface (articular surface $21_L$, $21_m$) of each condyle $18_{M,L}$ is defined by at least two different radii. In the figures, radius $R_{1HL}$ represents an inner (medial) radius of the lateral condyle $18_L$, while radius $R_{2HL}$ represents an outer (lateral) radius of the lateral condyle $18_L$. Similarly, radius $R_{1HM}$ represents an inner (medial) radius of the medial condyle $18_M$, while radius $R_{2HM}$ represents an outer (lateral) radius of the medial condyle $18_M$. It will therefore thus be appreciated that the radii of the condyles $18_{M,L}$ at the center of the implant are different than the radii at the outer (lateral) edges of the respective condyles (lateral edges of the implant).

The medial-lateral width of condyles $18_M$ and $18_L$ are defined by $W_{HM}$ and $W_{HL}$, respectively. The medial articular surface $21_M$ may not be equivalent to the lateral articular surface $21_L$ when the following conditions exist: radius $R_{1HM}$ does not be equal to $R_{1HL}$, radius $R_{2HM}$ does not be equal to $R_{2HL}$, and/or $W_{HM}$ does not equal $W_{HL}$.

The articular surface $31_L$, $41_L$ is created by revolving a single radius $R_{1UL}$ about axis 12 creating a concave surface (FIG. 14B). Thus, in one embodiment, the articular surface $31_L$ and $31_M$ (and $41_L$ and $41_M$) can be defined by the same radius (i.e., $R_{1UL} = R_{1UM}$) (see FIG. 14B).

An alternative embodiment of articular surface $31_L$, $41L$, as illustrated in FIGS. 14B and 14C, has instead two different radii $R_{1UL}$ (near midline $12a$) and $R_{2UL}$ (away from midline $12a$) that are revolved around joint axis 12 to create a concave surface. In the figures, radius $R_{1UL}$ represents an inner (medial) radius of the lateral surface $31_L$, $41_L$, while radius $R_{2UL}$ represents an outer (lateral) radius of the lateral surface $31_L$, $41_L$. Similarly, radius $R_{1UM}$ represents an inner (medial) radius of the medial surface $31_M$, $41_M$, while radius $R_{2UM}$ represents an outer (lateral) radius of the medial surface $31_M$, $41_M$. It will therefore thus be appreciated that the radii of the surface $31_{M,L}$ and $41_{M,L}$ at the center of the implant are different than the radii at the outer edges of the respective condyles (lateral edges of the implant).

The medial-lateral width of surfaces $31_M$ and $41_M$ is defined by $W_{UM}$. The medial-lateral width of surfaces $31_L$ and $41_L$ is defined by $W_{UL}$. The medial articular surfaces $31_M$ and $41_M$ may not be equivalent to the lateral articular surfaces $31_M$ and $41_M$, respectively when the following conditions exist: radius $R_{1UM}$ does not be equal to $R_{1UL}$, radius $R_{2UM}$ does not be equal to $R_{2UL}$, and/or $W_{UM}$ does not equal $W_{UL}$. As the two radii humeral condyle 18 embodiment pivots about respective two radii ulnar bearing surface 31,41 with an applied external moment, as seen in FIGS. 13 and 14C, the contact location on respective articulation shifts outwardly (away from midline $12a$) thereby gradually increasing the restoring moment.

The articular surfaces $31_{M,L}$ of unlinked ulnar bearing $5a$ are very similar to articular surfaces $41_{M,L}$. The unlinked bearing $5a$, however, has a raised distal face 32, as seen in FIG. 9, and extends further superiorly than linked bearing $5b$. As a result, the concavity opens up at these extending regions to increase range of motion of the elbow joint.

Accordingly, the articulation between the humeral condyles $18_{M,L}$ and ulnar bearings $5a,b$ in the coronal plane is not completely conforming as illustrated in FIGS. 13 and 14C. The ratios of $R_{1HL}/R_{1UL}$, $R_{1HM}/R_{1UM}$, $R_{2HL}/R_{2UL}$, and $R_{2HM}/R_{2UM}$ are approximately 0.85-0.98.

It will be understood that the top arrow in FIG. 13 describes an applied compressive force (F) across the joint, and the 2 bottom arrows describe the joint reaction force (F/2). As a varus moment (M+) (represented by the first curved arrow) is applied, the joint reaction force (F+) becomes greater on the medial side (longer bottom arrow) than the lateral side (shorter bottom arrow). As a greater varus moment (M++) (represented by the second curved arrow) is applied, the joint reaction force (F++) is completely on the medial side creating lift-off on the lateral side. In addition, the contact location of joint reaction force (F++) and shifts outwardly distance X as $R_{2HL}$ rolls onto $R_{2UL}$ as indicated in the rightmost figure of FIG. 13.

Thus, in accordance with one embodiment of the present invention, the bearing surfaces of the humeral condyles $18_{M,L}$ and ulnar bearings $5a,b$ are not toroidal in shape as in conventional designs but instead, each of the associated bearing surfaces has a cross-section in a coronal plane that exhibits at least two different radii. This construction provides for a shifting or migrating contact (in the lateral direction) between the two mating components during movement between the two components and provides for the advantages described herein.

Humeral Bushings for Linked Configuration

Figure 15:
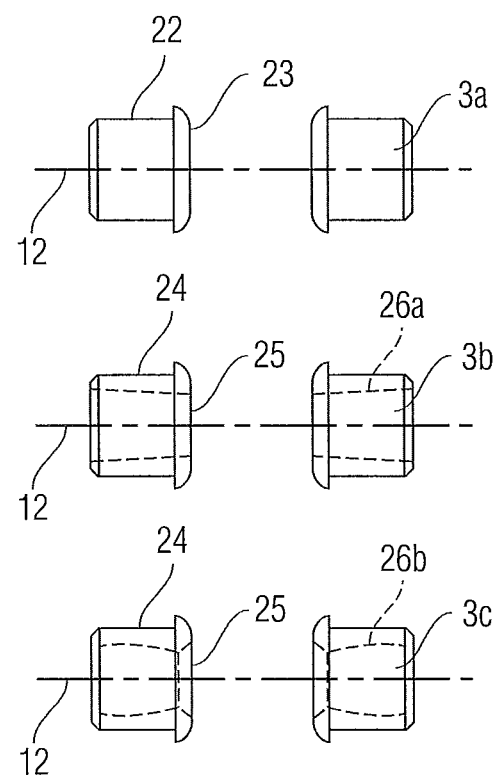
Figure 16:
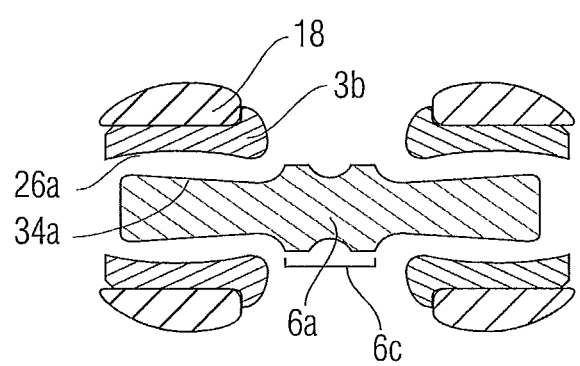
Figure 16:
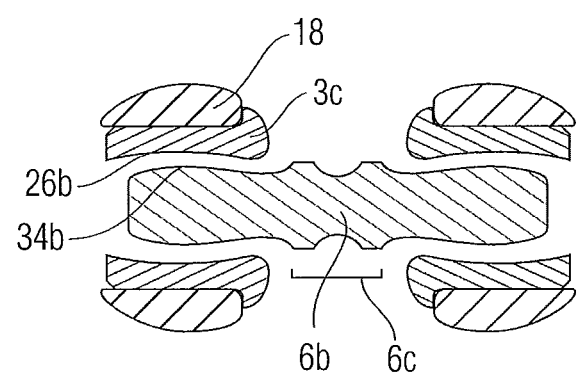
Figure 17:
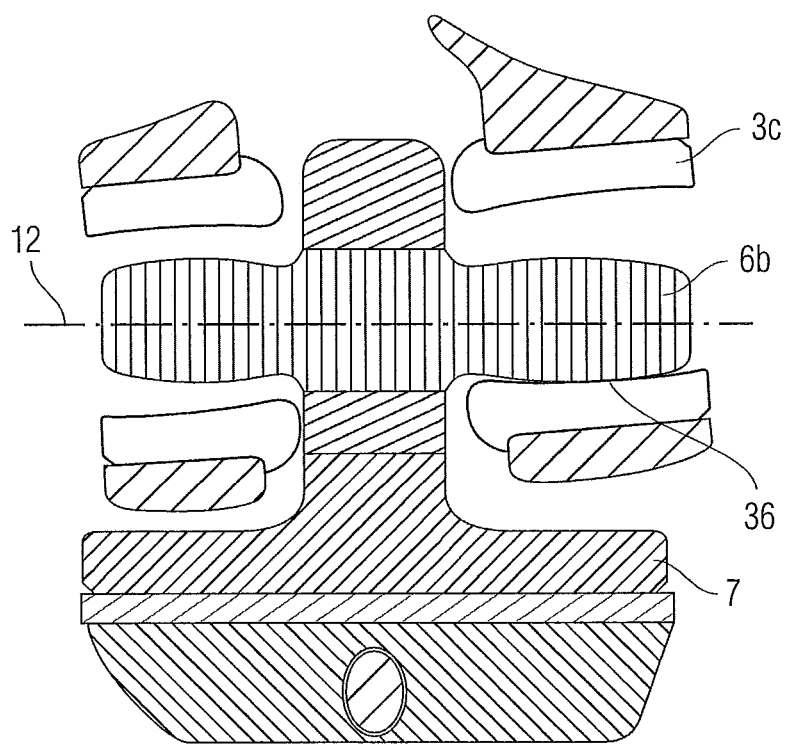
Figure 18:
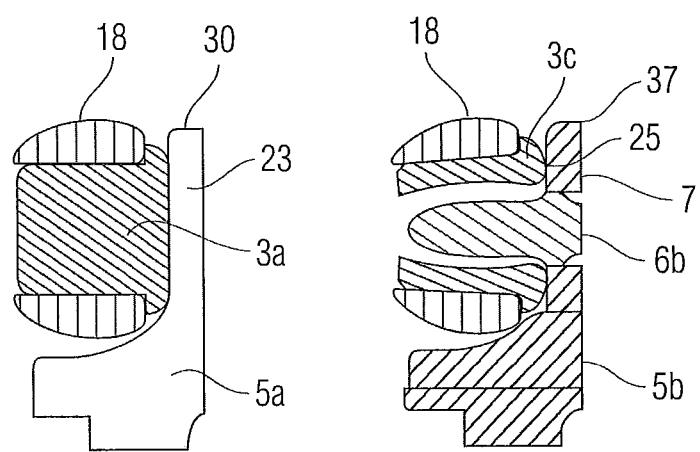

The humeral bushing $3b,c$, as illustrated in FIGS. 15 and 16 to be used in the linked total elbow configuration, has a cylindrical outer diameter 24 that is press-fit into the inner diameter 17 of medial $18_M$ or lateral humeral $18_L$ condyles. In one example, the inner diameter can be conical $26a$ to increase contact area when it contacts the end $34a$ of a conical-shaped axle $6a$. The cone angle of the conical axle $6a$ is less than the cone angle of the inner diameter $26a$ of conical bushing $3b$. In another example, the articulation 36 between the barrel-shaped bushing $3c$ and the barrel-shaped axle $6b$ is non-conforming. This curved articulation allows for improved contact pressure at all ranges of motion where axle $6b$ contacts bushing $3c$ as illustrated in FIG. 17. The bushing's central face 25 articulates with post 37 of the linked ulnar bearing housing during medial-lateral translation, as illustrated in FIG. 18. The bushing may be made of a low friction material, for example, ultra-high molecular weight polyethylene (UHMWPE).

Humeral Bushing Cap for Unlinked Configuration

The humeral bushing hole cap $3a$, as illustrated in FIG. 15, can be inserted into the cylindrical hole 17 of either the medial $18_M$ or lateral $18_L$ humeral condyle, and can be used in an unlinked total elbow configuration. The central face 23 of the cap articulates with the post 30 of the unlinked ulnar bearing $5a$ during medial-lateral translation, as illustrated in FIG. 18. Should the elbow be converted to a linked configuration, the caps $3a$ can be removed and discarded.

Figure 19:
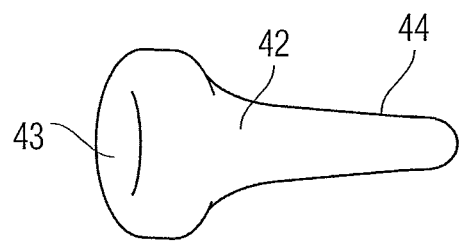

A radial head component 42, as illustrated in FIG. 19, has a proximal body 43 that articulates with the capitellum. The component 42 has a distal stem 44 that follows the axis of the shaft of the radius. The stem 44 is coated with plasma spray or porous metal and possibly hydroxyapatite to promote cementless fixation to bone.

A preferred overall carrying angle of the elbow replacement device is 10° where the ulna has 3° of carrying angle, and the humerus has 7°.

The range of motion of the device may be from 0-160° degrees of flexion.

The device can be imbedded with a material that resorbs over time in parallel with the time it takes for the native elbow soft tissue structures to heal. As the native elbow strengthens during the healing process, the resorption of the material causes the joint of the elbow replacement to become less stiff.

With regard to the unlinked design, the convex humeral condyles 18 articulate with a concave unlinked ulnar bearing surface 31. The articulation-adjustable ulnar stem 4 is allows for ulnar bearing $5a$ exchange if the component wears or if a different constraint type is needed. The ulnar bearing $5a$ can come in various thicknesses y to provide intra-operative adjustment of soft tissue constraint. The post 37 can come in various thicknesses δ to provide intra-operative adjustment of implant constraint. The ulnar bearing $5a$ is assembled to the ulnar stem 4 from approximately a medial and/or lateral direction in order to preserve the triceps attachment to the proximal ulna. Should the humeral component not have a modular condyle connection 19a and 19b, the bushings holes 17 can be capped-off 3a to allow the condyles 18 and the bushing cap central face 23 to articulate with the unlinked ulnar bearing 5a.

With regard to the linked design, each convex humeral component condyle 18 has cylindrical holes 17 along the same axis that capture press-fit humeral bushings 3b,c. The linked ulnar bearing housing 7 is assembled to ulnar stem 4 from approximately a medial and/or lateral direction by means of a sliding capture mechanism 28 to preserve the triceps attachment to the proximal ulna. The linked, convex ulnar bearing 5b engages with the ulnar bearing housing 7 and can be revised if, for example, the bearing surface wears over time. The axle 6 rigidly locks to the ulnar bearing housing 7 using, for example, a locking component 9. The humeral articular surfaces engage the ulnar articular surfaces in sequence (FIGS. 17 and 18): 1. Upon varus/valgus rotation, the medial and/or lateral humeral condylar surfaces 21 $_{M,L}$ articulate with the medial and/or lateral bearing surfaces 41 of the linked ulnar bearing, respectively. 2. With further rotation, lift-off of one humeral condyle from one ulnar bearing surface occurs, and the axle 6 articulates with the inner surfaces 26 of the humeral bushings 3b,c. 3. Upon further rotation and medial-lateral translation, the central faces 25 of the humeral bushings 3b,c articulate with the post 37 of the linked ulnar bearing housing.

The surgical technique for implanting in a patient the elbow replacement device disclosed herein avoids taking down the triceps. A medial or lateral approach can be used to implant the device. The approach is not minimally invasive, but rather soft tissue preserving. The lateral soft tissue structures are preserved. The distal humeral epicondyles can be retained. Resection of the radial head is optional.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. An elbow prosthesis comprising:
a humeral component having a distal end and a proximal end, the proximal end having a humeral stem and the distal end including two distally extending condylar portions, each distally extending condylar portion having a hole extending therethrough and a condylar articulating surface;
an ulnar component having a distal end and a proximal end, the distal end having an ulnar stem and the proximal end having an ulnar bearing component, the ulnar bearing component comprising complementary bearing surfaces that mate and articulate with the condylar articulating surfaces, the ulnar bearing component further including a central post extending between the two distally extending condylar portions that provides medial-lateral stability to the elbow prosthesis;
an axle that is connected to the post of the ulnar component, wherein the two distally extending condylar portions rotate about the axle; and
a humeral bushing assembly that includes a pair of humeral bushings that are received within the holes of the distally extending condylar portions of the humeral component; wherein the axle passes through the humeral bushings and through an opening formed in the post for detachably linking the humeral component to the ulnar component,
wherein the axle includes a first end portion and an opposite second end portion, wherein each of the first and second end portions has a cross-sectional diameter that changes along a length of the respective end portion creating a barrel-shaped end portion with a central portion disposed therebetween, wherein the first and second barrel-shaped end portions are disposed on opposite sides of the post of the ulnar bearing component with the central portion of the axle being fixedly locked to the post.

2. The elbow prosthesis of claim 1, wherein the first and second barrel-shaped end portions articulate with inner surfaces of the humeral bushings.

3. The elbow prosthesis of claim 1, wherein the ulnar component includes a structure at the proximal end of the ulnar component for engagement with the ulnar bearing component to permit the ulnar bearing component to be detachably coupled to the ulnar component, thereby, allowing the ulnar bearing component to be removed even when the ulnar component is fixedly attached to the ulna of a patient.

4. The elbow prosthesis of claim 1, wherein the ulnar bearing component slidingly attaches to the ulnar component.

5. The elbow prosthesis of claim 1, wherein each of the condylar articulating surfaces is defined by a single convex radius as measured in a coronal plane.

6. The elbow prosthesis of claim 1, wherein each of the condylar articulating surfaces has a cross-section in a coronal plane that exhibits at least two different tangent convex radii, the ulnar bearing component having complementary bearing surfaces that mate with the articulating surfaces of the distally extending condylar portions, wherein each of the bearing surface of the ulnar bearing component has a cross-section in a coronal plane that exhibits at least two different tangent concave radii.

7. The elbow prosthesis of claim 6, wherein an inner radius of each of the articulating surfaces of the distally extending condylar portions is less than an outer radius thereof.

8. The elbow prosthesis of claim 1, wherein the condylar articulating surfaces of the distally extending condylar portions and the ulnar bearing component are configured such that varus and valgus rotation of the humeral component relative to the ulnar bearing component causes a contact point between the humeral component relative to the ulnar bearing component to move outwardly.

9. The elbow prosthesis of claim 1, wherein the humeral component comprises a modular structure comprising a proximal part that includes the humeral stem and a distal part that includes the condylar portions, wherein at least one of the proximal part and the distal part has a cavity at one end for receiving an extension formed at an end of the other of the proximal part and the distal part to thereby establish modularity and permit the humeral condylar portions to be removed even when the proximal part is fixedly attached to the humerus of the patient.

10. The elbow prosthesis of claim 1, wherein each of the distally extending condylar portions of the humeral component includes at least one suture hole for soft tissue/bone attachment and on an postero-lateral aspect of the distally extending condylar portion of the humeral component adjacent to a lateral condyle thereof, a concave recess is formed to contain any lateral bone fragments.

* * * * *